United States Patent
Cloetta et al.

(10) Patent No.: US 10,046,877 B2
(45) Date of Patent: Aug. 14, 2018

(54) ELECTRON BEAM GENERATOR AND ELECTRON BEAM STERILIZING DEVICE

(71) Applicant: Tetra Laval Holdings & Finance S.A., Pully (CH)

(72) Inventors: Dominique Cloetta, Villars-sur-Glâne (CH); Urs Hostettler, Thun (CH); Werner Haag, Lugnorre (CH); Simone Bianco, Bern (CH)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/127,895

(22) PCT Filed: Mar. 9, 2015

(86) PCT No.: PCT/EP2015/054812
§ 371 (c)(1),
(2) Date: Sep. 21, 2016

(87) PCT Pub. No.: WO2015/139982
PCT Pub. Date: Sep. 24, 2015

(65) Prior Publication Data
US 2017/0183115 A1    Jun. 29, 2017

(30) Foreign Application Priority Data
Mar. 21, 2014 (SE) ...................... 1450331

(51) Int. Cl.
*B65B 55/00* (2006.01)
*B65B 55/08* (2006.01)
(Continued)

(52) U.S. Cl.
CPC .............. *B65B 55/08* (2013.01); *A61L 2/087* (2013.01); *A61L 2/26* (2013.01); *H01J 29/04* (2013.01);
(Continued)

(58) Field of Classification Search
CPC . B65B 55/08; A61L 2/087; A61L 2/26; A61L 2202/11; A61L 2202/23; H01J 29/04; H01J 37/06
(Continued)

(56) References Cited

U.S. PATENT DOCUMENTS 3,906,601 A    9/1975  Buescher et al.
4,268,776 A    5/1981  Morrison
(Continued)

FOREIGN PATENT DOCUMENTS

WO    WO 2010/040453 A1    4/2010
WO    WO 2013/154782 A1    10/2013

OTHER PUBLICATIONS

*International Search Report (PCT/ISA/210) dated May 11, 2015, by the European Patent Office as the International Searching Authority for International Application No. PCT/EP2015/054812.
(Continued)

*Primary Examiner* — Nicole Ippolito
*Assistant Examiner* — Hanway Chang
(74) *Attorney, Agent, or Firm* — Buchanan Ingersoll & Rooney PC

(57) ABSTRACT

Electron beam generator comprising an electron emitting device adapted to emit an electron beam when heated to an elevated temperature, wherein the electron emitting device comprises a filament having a spiral portion.

16 Claims, 6 Drawing Sheets

(51) Int. Cl.
 *A61L 2/08* (2006.01)
 *A61L 2/26* (2006.01)
 *H01J 37/06* (2006.01)
 *H01J 29/04* (2006.01)

(52) U.S. Cl.
 CPC .......... *H01J 37/06* (2013.01); *A61L 2202/11* (2013.01); *A61L 2202/23* (2013.01)

(58) Field of Classification Search
 USPC ............................. 250/492.1, 492.2, 492.3
 See application file for complete search history.

(56) References Cited

U.S. PATENT DOCUMENTS

| | | |
|---|---|---|
| 5,864,199 A | 1/1999 | Alvis et al. |
| 6,707,240 B1 | 3/2004 | Nakasuji et al. |
| 8,264,134 B2 | 9/2012 | Tunna et al. |
| 2010/0239828 A1 | 9/2010 | Cornaby et al. |
| 2011/0192986 A1 | 8/2011 | Holm et al. |
| 2015/0056095 A1 | 2/2015 | Gorzen et al. |

OTHER PUBLICATIONS

*Office Action issued by the Swedish Patent Office dated Oct. 8, 2014 in Swedish priority Application No. 1450331-2 (5 pgs).

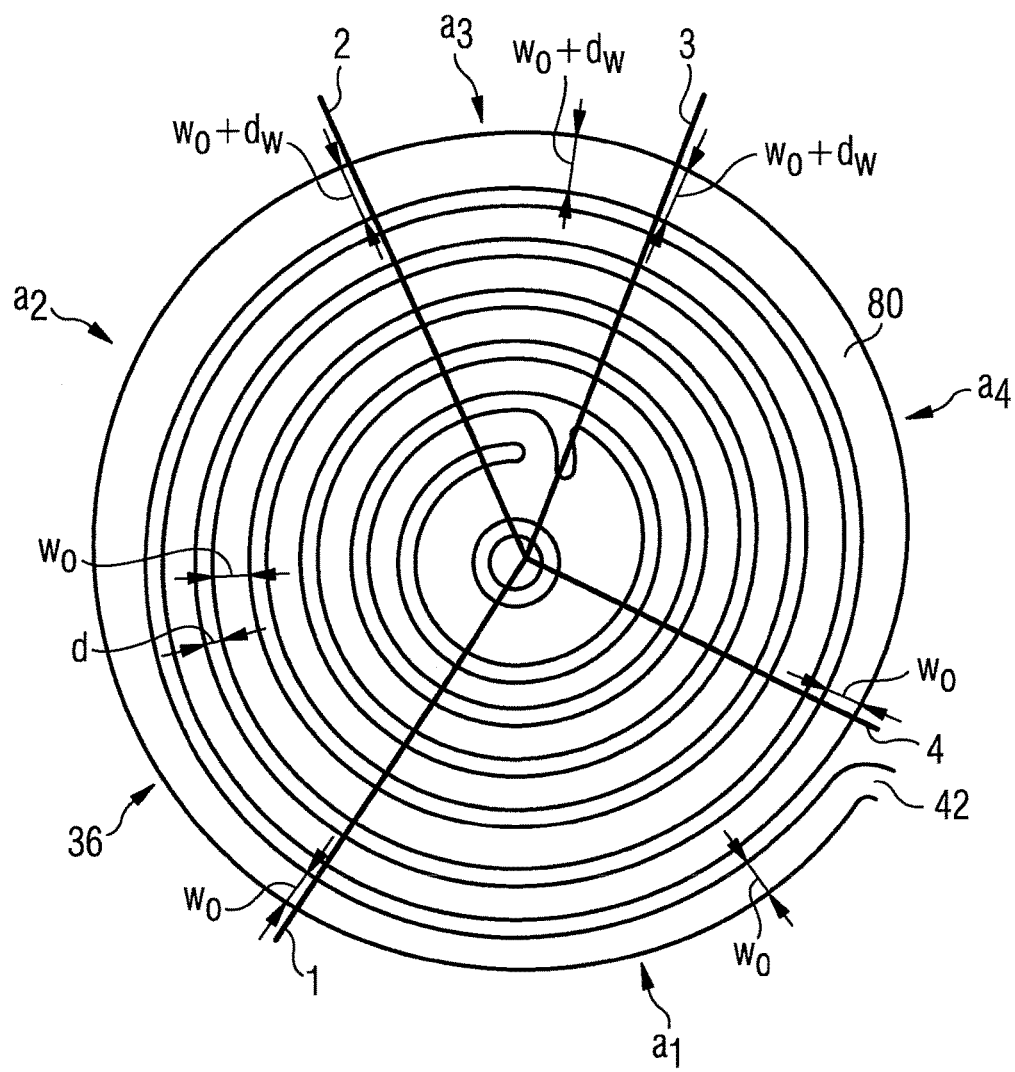

ELECTRON BEAM GENERATOR AND ELECTRON BEAM STERILIZING DEVICE

The invention relates to an electron beam generator and an electron beam sterilizing device for sterilizing a packaging container by electron beam irradiation.

It is common practice to pack food products and drugs, including liquid and partly liquid products, in packaging containers. Such packaging containers may for example be manufactured from a laminate comprising at least one layer of paper or paperboard and one or more barrier layers, for example an aluminium foil and/or a polymer material, such as for example a polyethylene layer.

In particular in the medical and food industry, packaging containers are sterilized before they are filled with the product. Thereby, microorganisms, such as bacteria, fungi, viruses and spores, which may be present on a surface of the packaging container, are eliminated.

A known method of sterilizing packaging containers is through radiation by charge carriers, in particular electron beams. A known electron beam sterilizing device comprises an electron beam generator arranged in a vacuum housing which is provided with an electron exit window. The electron beam generator comprises a filament connected to an electrical power supply. When an electrical current is fed through the filament, the electrical resistance of the filament causes the filament to be heated to an elevated temperature, such as in the order of 2000 K. This heating causes the filament to emit a cloud of electrons. The electrons are accelerated towards the electron exit window by means of a high-voltage potential between a cathode near the filament and the electron exit window (being the anode). Due to the high energy of the electrons, the electrons pass through the electron exit window towards a target area, i.e. a surface of the packaging container to be sterilized.

There are electron beam sterilization devices, or emitters, which can be lowered into a packaging container for sterilizing the interior of the packaging container. A known electron beam sterilizing device adapted for an interior sterilization of a packaging container comprises a generally tubular housing adapted to be at least partly inserted into a packaging container. The electron exit window is arranged on a front end of the tubular housing and has a generally circular shape. The filament is arranged in the housing, i.e. the vacuum chamber, and generates an electron beam which is then directed by means of a high voltage potential towards the electron exit window.

A known filament for an electron beam sterilizing device is ring-shaped. Such a ring-shaped filament generates a beam profile having a central peak and a declining current density in a radial direction. In this connection, the term "beam profile" relates in particular to the beam intensity profile in a direction perpendicular to the direction of propagation of the electron beam, more particularly to the current intensity or current density along the radius of the electron exit window.

In order to generate a more even or homogeneous beam profile, it is known to place a beam-shaping grid between the filament and the electron exit window in order to shape the electron beam. A beam-shaping grid comprises a plurality of openings and is in particular used for diffusing the electron beam into a more uniform beam and for focusing the electron beam towards the electron exit window.

An electron beam sterilizing device with an electron beam shaping grid is disclosed in U.S. 2011/0192986 A1. The grid is connected to a voltage supply. By applying or not applying a positive or negative voltage to the grid, the electrons formed at the filament will exit the grid or not. The grid comprises at least two operational portions in order to shape the beam profile.

It is an object of the present invention to provide an electron beam generator and an electron beam sterilizing device generating an electron beam having an essentially homogeneous beam profile, in particular without using a control grid.

The object is solved according to the invention with an electron beam generator according to claim 1 and an electron beam sterilizing device according to claim 11. Preferred embodiments are defined in the dependent claims and the following description, in particular taken together with the attached drawings.

The electron beam generator comprises an electron emitting device adapted to emit an electron beam when heated to an elevated temperature, such as in the order of 2000 K, e.g. at least 1800 K. The electron-emitting device has a substantially flat shape and comprises a filament having a spiral portion, which preferably extends between an outer portion and an inner portion of the flat electron-emitting device.

The electron beam sterilizing device according to the invention is adapted for sterilizing a packaging container, in particular an interior of a packaging container, by electron beam irradiation. The electron beam sterilizing device comprises a housing enclosing an internal space, wherein the housing comprises an electron exit window. An electron beam generator according to the invention is arranged in the internal space for generating an electron beam. The electron beam exits the housing through the electron exit window for sterilizing the packaging container.

A first aspect of the invention is to provide an electron emitting device, which can also be described as generally disc-shaped. The electron emitting device is preferably a substantially circular plate having free spaces formed therein. The disc-shaped electron emitting device preferably has a thickness max. 0.3 mm, preferably max. 0.2 mm. The thickness is preferably homogenous (except for any through-going slit or opening). A diameter of the electron-emitting device is preferably at least 1 cm, more preferably in the order of a few centimeters, such as between 1.5 cm and 5 cm.

A second aspect of the invention is to provide a spiral filament within the disc-shaped electron emitting device. In other words, the disc-shaped electron emitting device comprises a spiral portion. The spiral portion (filament) itself has a flat shape, i.e. not a circular cross-section, but a rectangular cross section. The disc-shaped emitter preferably comprises a spiral slit formed in the material of the disc, thereby forming the flat, spiral filament in the disc-shaped electron emitting device. The inventive electron emitting device can also be described as a disc having at least one slit formed therein, such that on a portion of the disc, a spiral filament is formed. The spiral filament generates a substantially homogeneous beam profile and, therefore, a homogeneous temperature at the electron exit window.

In an embodiment of the invention, the electron emitting device comprises a flat outer support element connected to an outer end of the spiral filament. In other words, the spiral filament does not extend over the entire radius of the flat electron emitting device, but merges at its outer end into a support element, which is preferably ring-shaped. This outer support element, or support ring, may have a radial extension at least a few times larger than the radial extension (width) of the windings of the filament. Due to its size, and therefore its lower temperature compared to the spiral portion of the electron beam generator, the support ring normally does not emit electrons when the electron beam generator is operated. In other words, the size of the support ring is such that it does not emit electrons when the electron beam generator is operated. During operation, an electron current between 1 Milliampere (mA) and 10 mA, preferably 1 mA to 4 mA, is emitted by the electron emitting device, in particular the filament. The electrical power applied to the electron emitting device may be the order of 100 watts (W) to 400 W. In larger electron emitting devices an electron current between 4 mA and 6 mA may be emitted by the filament. The electrical power applied is then about 300-500 W.

The outer support element, or support ring, is preferably adapted to support the electron emitting device. In one embodiment of the invention, the outer support element comprises at least one connecting portion for mechanically and/or electrically connecting the electron emitting device. For example, 1, 2, 3 or more connecting portions may be provided at the outer support element. The connecting portions are preferably distributed in a circumferential direction on the outer support element. The connecting portions may be any interface for mechanically mounting a supporting structure, such as a supporting rod. For example, the outer support element may have one or more apertures for connecting (receiving) a supporting rod. Another alternative is to weld the outer support element to the support housing in a number of points. The inner support element may be welded to a pin connected to the support housing.

In another embodiment of the invention, a gap is formed in the outer support element. The gap, or hole, is preferably formed in a portion of the outer support element adjacent to a connecting portion of the filament, where the filament merges into, or connects to, the outer support element. In particular, the gap may be formed in a portion of the outer support element radially outward of the outer connecting portion of the filament. The gap formed in this area causes the temperature in an area of the outer support element near the connecting portion of the filament to be higher, due to less material in this area. This causes the beam profile to not abruptly decline at the outer end of the spiral filament. Therefore, a more homogeneous profile can be achieved, in particular in a radially outer portion.

The gap may be formed as a slit which preferably extends in the circumferential direction of the outer support element. The gap forms, or generates, a rib-like structure between an inner border, or edge, of the outer support element and the gap (opening) itself. The length of the slit may be in the order of 10° to 180°, in particular 20° to 60°.

In an embodiment of the invention, the filament comprises a plurality of windings, wherein a distance between the windings in a radial direction is equal to or smaller than a radial extension (width) of the windings. In other words, the width of the windings is equal to or larger than the width of the slits between the windings. By minimizing the slit size, the uniformity of the beam profile can be further enhanced.

In another embodiment of the invention, the distance between an outer winding of the filament and the outer support element is larger than a distance between adjacent windings of the filament.

The filament may comprise 3 to 8 windings, in particular 3 to 6, 3 to 5 or 3 to 4 windings. If the number of windings increases, the filament power necessary for a certain emission current must be increased and the efficiency decreases therefore. A preferred material of the electron-emitting device, in particular the filament, is tungsten.

In an embodiment of the invention, an outer connection point, or connecting portion, of the filament, where the filament is connected to the outer support element, is displaced, in the circumferential direction, relative to an inner connection point, or portion, of the filament, where the filament is connected to an inner support element. The circumferential offset of the connecting points of the filament to the inner and outer support element provides a more uniform beam profile in the circumferential direction.

According to another embodiment, the filament comprises a connecting portion, which merges into an inner support element and/or an outer support element, wherein the connecting portion comprises a bend, or curve, in particular between a radial and a circumferential direction. In other words, the filament comprises a spiral portion and a connecting portion, wherein the connecting portion is arranged between the spiral portion and the inner support element and/or the outer support element and comprises a bend. Therefore, the spiral part of the filament does not merge into the respective support element in a straight manner, but bends towards the support element.

In another embodiment of the invention, the spiral portion of the filament has a constant width along its longitudinal extension. The constant width or constant radial extension further provokes the homogeneous beam profile.

In another preferred embodiment, the electron-emitting device comprises an inner, preferably flat support element connected to an inner end of the filament. The inner support element may have a radial extension at least a few times larger than the radial extension (width) of the windings of the filament. Due to its size, and therefore its lower temperature compared to the spiral portion of the electron beam generator, the inner support element normally does not emit electrons when the electron beam generator is operated.

The inner support element is preferably adapted to support the electron emitting device. In one embodiment of the invention, the inner support element comprises at least one connecting portion for mechanically and/or electrically connecting the electron emitting device. The connecting portion may be any interface for mechanically mounting a supporting structure, such as a supporting rod, such as an aperture formed in the inner support element. The inner support element may in particular be a support ring.

The inner support element is preferably disc-shaped or ring-shaped. The inner support element may in particular be a whole disc without slits. In another embodiment, a slit or hole may be provided in the inner support element. The hole, in particular through-hole, is preferably formed centrally in the inner support element. The hole causes the temperature in an area of the outer support element near the connecting portion of the filament to be higher, so that the beam profile does not abruptly decline at the inner end of the spiral filament. Therefore, a more homogeneous profile can be achieved, in particular in a radially inner portion.

According to another aspect of the invention, the electron emitting filament is integrally formed with an inner support element, in particular plate or ring, and an outer support element, in particular ring, and exclusively supported by the inner and outer support elements. Inner and outer support element and filament may be formed together as a disc, preferably having a constant thickness.

In one or more embodiments the spiral portion of the filament has a varying width along its longitudinal extension. In particular, in one or more embodiments at least an outer winding of the spiral portion has a varying width along its longitudinal extension. In this way the temperature can be adjusted for angular sections of the filament in such a way that an electron beam is achieved which is homogenous over the window, with only small variations between angular sectors of the spiral portion, and with a correct radial distribution of the electrons. The electron emission, i.e. the amount of electron generated, within each angular sector is similar. It will depend both on the emitting surface area available and the temperature of that area.

In the following, the invention will be further described in connection with the attached drawings, in which:

FIG. 7b shows a portion of the embodiment of FIG. 7a, but in an exaggerated version.

Equal or corresponding elements are denominated with the same reference numerals in all figures. Features described in connection with different figures can be combined as far as technically possible.

FIG. 5 shows an electron beam sterilizing device 10 according to the invention for an interior sterilization of a packaging container, in particular a food or drug container.

Figure 5:
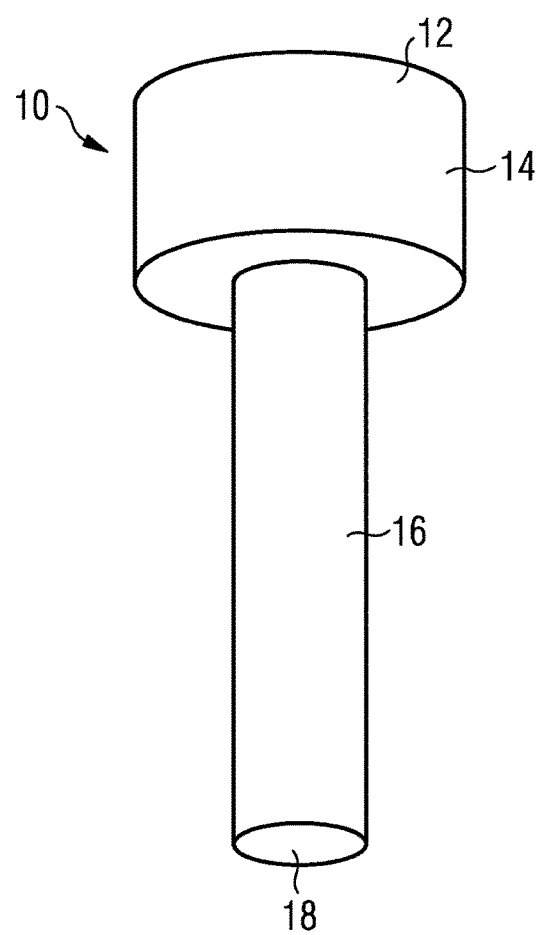
FIG. 5 shows an electron beam sterilizing device according to the invention comprising an inventive electron beam generator.
Figure 6:
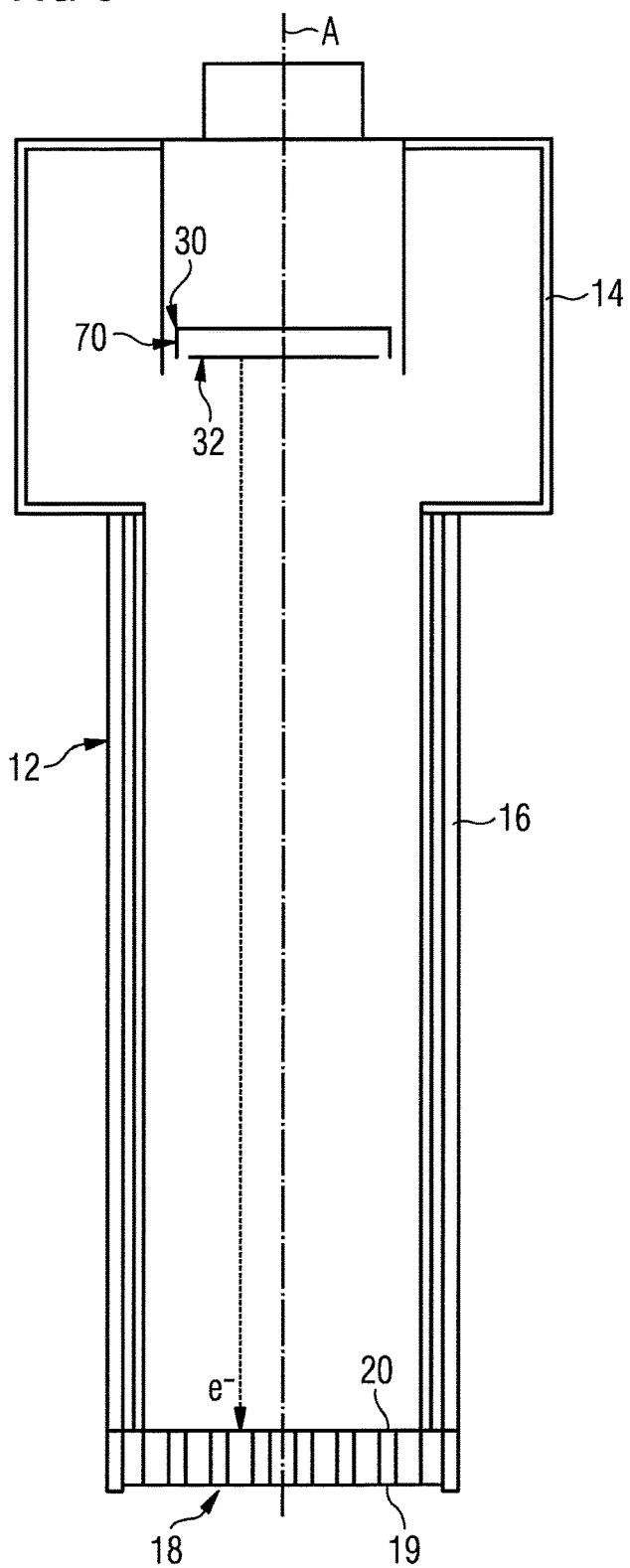
FIG. 6 shows a cross section of the electron beam sterilizing device of FIG. 5.

In FIGS. 5 and 6 the electron beam sterilizing device 10 is shown. The electron beam sterilizing device 10 comprises a housing 12 enclosing an internal space, in particular a vacuum space. The housing 12, or vacuum chamber, has a substantially cylindrical shape being axis-symmetric around longitudinal axis A. The housing 12 comprises a first housing portion 14, in which an inventive electron beam generator 30 is positioned, and a cylindrical or tubular second housing portion 16 adapted to be inserted into a packaging container so as to sterilize an interior of the container. An electron exit window 18 is formed on a front end of the second housing portion 16, opposite the first housing portion 14. The electron exit window 18 comprises an electron transparent foil 19 and a foil support member 20. An electron acceleration zone is formed between the electron beam generator 30 and the electron exit window 18, in particular within and along the second housing portion 16. The acceleration zone is illustrated by the travelling path of a single electron e⁻.

The electron beam generator 30 arranged in the vacuum housing 12, in particular the first housing portion 14, is adapted to generate a cloud of electrons, which is accelerated towards the electron exit window 18, when heated to an elevated temperature, in particular in the order of 2000 K. Embodiments of the electron beam generator 30 according to the invention will now be described with reference to FIGS. 1 to 4.

Figure 1:
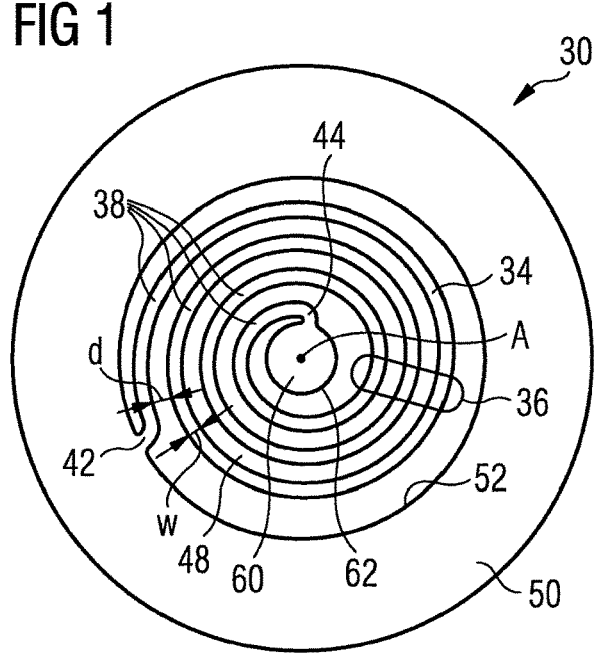
FIG. 1 shows a first embodiment of an electron beam generator according to the invention.

FIG. 1 shows a first embodiment of an electron beam generator 30 according to the invention. The electron beam generator 30 comprises an electron emitting device 32 being integrally formed in a flat, disc-like shape. The electron-emitting device 32 may have a diameter of a few centimeters, such as at least two, at least three or at least five centimeters. A thickness of the electron-emitting device 32 can be in the range of 0.05 millimeters to 0.15 millimeters. Preferably, the thickness of the electron-emitting device 32 is 0.2 millimeters or below. The thickness may vary along the radius of the electron-emitting device 32, however, the thickness will generally be constant throughout.

The electron-emitting device 32 comprises a filament 34 and support elements 50, 60. The filament has a generally spiral shape. The filament 34 comprises a plurality of windings 38. An outer support element 50 surrounds the filament 34. The filament 34 is connected to the outer support element 50 at the first, outer connecting portion 42 disposed at a first (outer) end of the filament 34. The outer support element 50 surrounds the filament 34 and is preferably integrally formed with the filament 34. Filament 34 and outer support element 50 are arranged in a common plane (level).

A second longitudinal end (inner end) of the filament 34 is connected to an inner support element 60 having a disc-like shape. The inner support element 60 is preferably integrally formed with the filament 34 and connected to the filament 34 at a second, inner connecting portion 44. The filament 34, the outer support element 50 and the inner support element 60 are preferably made of tungsten.

The outer support element 50 and the inner support element 60 are configured to support the filament 34 by connecting to the respective longitudinal ends of the filament 34. The filament 34 is preferably supported exclusively by the outer support element 50 and the inner support element 60. In other words, the filament 34 is only supported at its respective longitudinal ends. Due to the size of the outer support element 50 and the inner support element 60, the temperature of the outer support element 50 and the inner support element 60 will be significantly lower than the temperature of the filament 34, in particular such that only a little or basically no electrons are emitted by the outer support element 50 and the inner support element 60.

The filament 34 comprises a spiral portion 36 and a first connecting portion 42 connecting to the outer support element 50 and a second connecting portion 44 connecting to the inner support element 60. The first connecting portion 42 has a bend turning towards the outside for connecting the spiral portion 36 to an inner border 52 of the outer support element 50, which is in particular circular. The second connecting portion 44 has a bend turning towards the inside for connecting the spiral portion 36 to an outer border 62 of the inner support element 60, which is in particular circular.

The first connecting portion 42 is displaced in the circumferential direction relative to the second connecting portion 44. In other words, the number of windings 38 of the filament 34 is not an integer. The filament 34 includes a plurality of full windings 38 and one fraction of a winding 38, wherein the fraction is preferably between 20% and 80% of a full winding 38. In a preferred embodiment, the displacement between the first connecting portion 32 and the second connecting portion 44 in the circumferential direction is between 45° and 75°.

Between each of the windings 38, a free space, distance or clearance 48 is formed. As can be seen in FIG. 1, the clearance 48 has a size approximately equal to the size of the windings 38. The term "size" refers in this case in particular to the width, i.e. the extension in the radial direction. For the distances or clearances 48 the width is denoted d in the drawings, whereas for the windings 38 the width is denoted w in the drawings. It may be preferred that the size, i.e. the distance d, of the clearance 48, is smaller than the size, i.e. the width w, of the windings 38.

Figure 2:
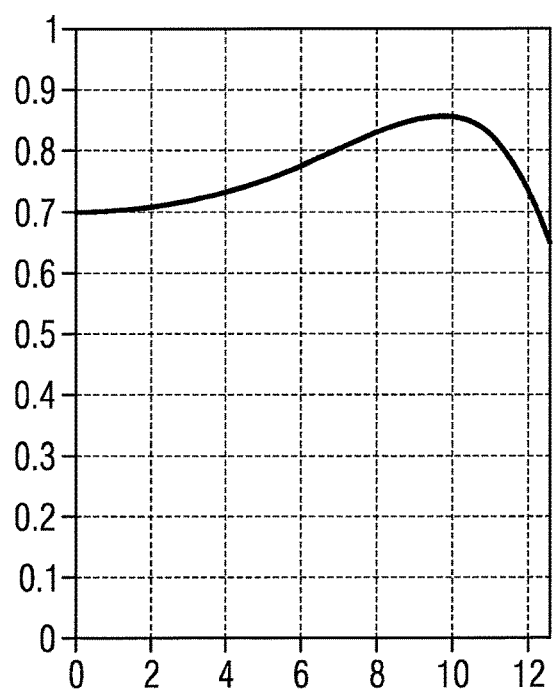
FIG. 2 shows a beam profile generated by the electron beam generator according to FIG. 1.

A beam profile that can be achieved with the electron beam generator 30 according to FIG. 1 is shown in FIG. 2. Because the beam profile is substantially symmetrical with regard to the central point of the electron beam generator 30, it is only shown along a radius on the exit window. The origin is in the center of the exit window. The graph represented in FIG. 2 refers to the dose measured on the electron exit window 18 of an electron beam sterilizing device 10. The centre of the electron-emitting device 32 is not emitting, because the temperature there is low. With increasing distance from the centre, the temperature increases and reaches its maximum value at a certain point of the filament 34 along its longitudinal extension. The temperature then decreases at an end of the filament 34 close to the outer support element 50. The decreased emission in the centre is a welcome effect, because it compensates the electrons scattered towards the centre. The intensity measured at the electron exit window 18 is essentially homogeneous along the radius of the electron exit window 18 but comprises a peak near the outer circumference of the electron exit window 18.

The diameter of the spiral portion 36 determines the diameter of the beam profile together with the design of the housing 12, in particular the second housing portion 16 (snout). In one embodiment the diameter of the filament 34 (corresponding to the inner diameter of the outer support element 50) corresponds to the diameter of the electron exit window 18. In other words, the outer support element 50 has a diameter greater than the diameter of the electron exit window 18.

The size of the clearances 48 between adjacent windings 38 (slit size) determines how much and how many electrons are scattered and how much current from the back side of the electron-emitting device 32 can get to the second housing portion 16 (tube). It has been found that the configurations shown in FIGS. 1 and 3 provide an advantageous configuration.

Figure 3:
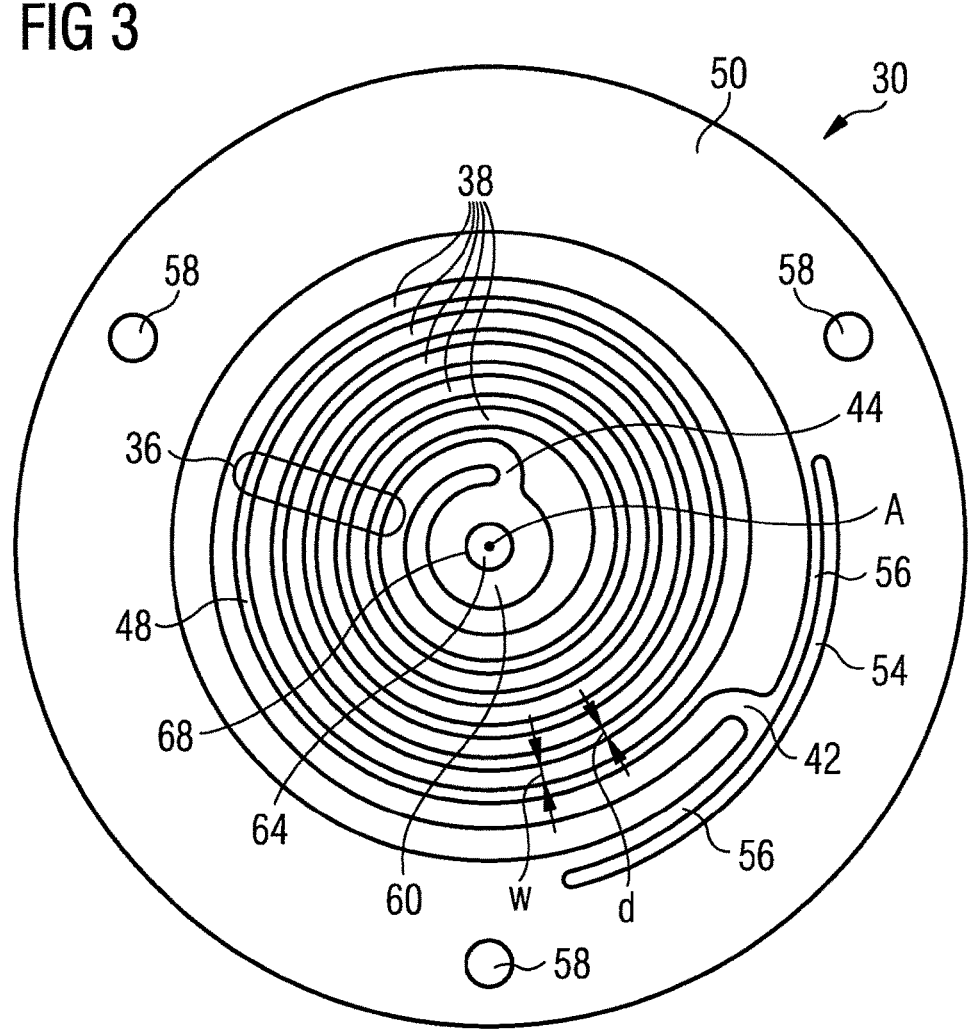
FIG. 3 shows a second embodiment of an electron beam generator according to the invention.

A second embodiment of an electron beam generator 30 is shown in FIG. 3. The embodiment essentially corresponds to the embodiment shown in FIG. 1 and only the differences will be described. The outer support element 50 comprises a gap 54 (air gap) which is located in a portion of the outer support element 50, where the filament 34 merges into the outer support element 50. The gap 54 is formed as a slit extending in the circumferential direction, such that the filament 34 branches into two ribs, or fins, 56. The size of these ribs 56 is such that a temperature is higher than the temperature of the remaining outer support elements 50, when the electron beam generator 30 is operated. Therefore, the temperature at the outer end of the filament 34 does not drop abruptly at the point where it merges into the outer support element 50. Preferably, the width of the ribs 56 essentially corresponds to the width of the windings 38 of the filament 34. The extension of the gap 54, or slit, in the circumferential direction is between 45 and 135°, preferably, about 90°. The gap 54 is arranged in a portion radially outward of the first connecting portion 42 of the filament 34, such that the filament 34 branches out at an outer end thereof. In other words, the outer support element 50 comprises two rib-like structures, adjacent the first connecting portion 42 of the filament 34.

The inner support element 60 also comprises a gap, i.e. a hole 64. The hole 64 is disposed in the centre of the inner support element 60, such that the inner support element 60 has a circular shape. The centre of the hole is aligned with the axis A. The central hole of the inner support element 60 is used for a central support bar 72, which will be described below. Due to the small width at the second connecting portion 44, compared to the inner support element 60, the temperature at the second connecting portion 44 will be higher.

Figure 4:
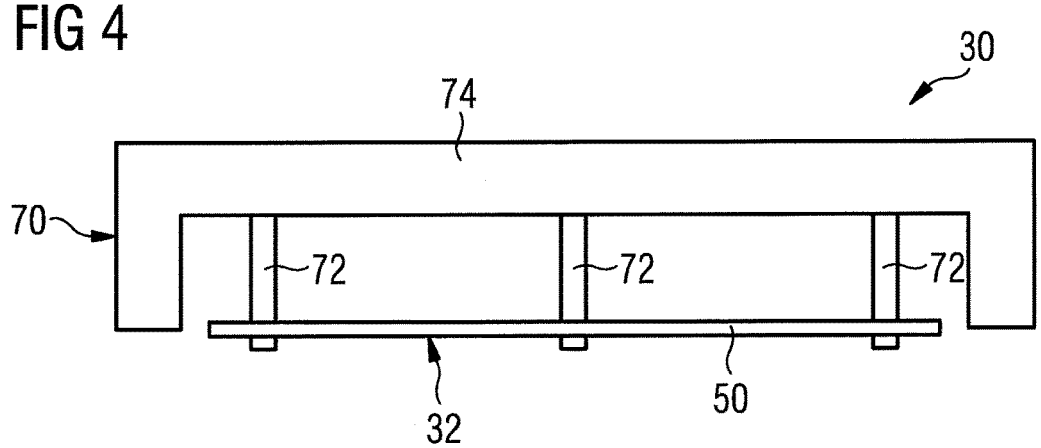
FIG. 4 shows a side view of an embodiment of an electron beam generator according to the invention.

The disc-like electron emitting device 32 is supported by a support structure 70, as shown in FIG. 4. The support structure 70 comprises a support housing 74 and a plurality of support bars, or rods, 72. A central support bar 72 is connected to the inner support element 60, and one or more outer support bars 72 are connected to the outer support element 50. For the respective connections, the outer support element 50 comprises one or more connecting points 58 and the inner support element 60 comprises at least one connecting point 68. The connecting points 58, 68 can be holes in the outer support element 50 and the inner support element 60. An electrical connection for operating the electron beam generator may be routed along, or through, the support bars 72. This support structure 70 is valid for all the embodiments. Another connection alternative is welding, i.e. the outer support element is welded to the support housing in a number of points. In the figure the disc-shaped electron emitting device 32 is planar, i.e. the disc is planar, i.e. it extends in a plane. However, it should be noted that the disc-shaped electron emitting device should be positioned in the support structure in a way to get an optimal configuration at operational temperatures. An optimal configuration of the disc-shaped electron emitting device is not necessarily perfectly planar. It may be necessary to position the disc-shaped electron emitting device in a non-planar way in room temperature to compensate for thermal dilatation at operational temperatures. Hence, the disc-shaped electron emitting device may be positioned in the support structure in a concave or convex manner.

Figure 7A:
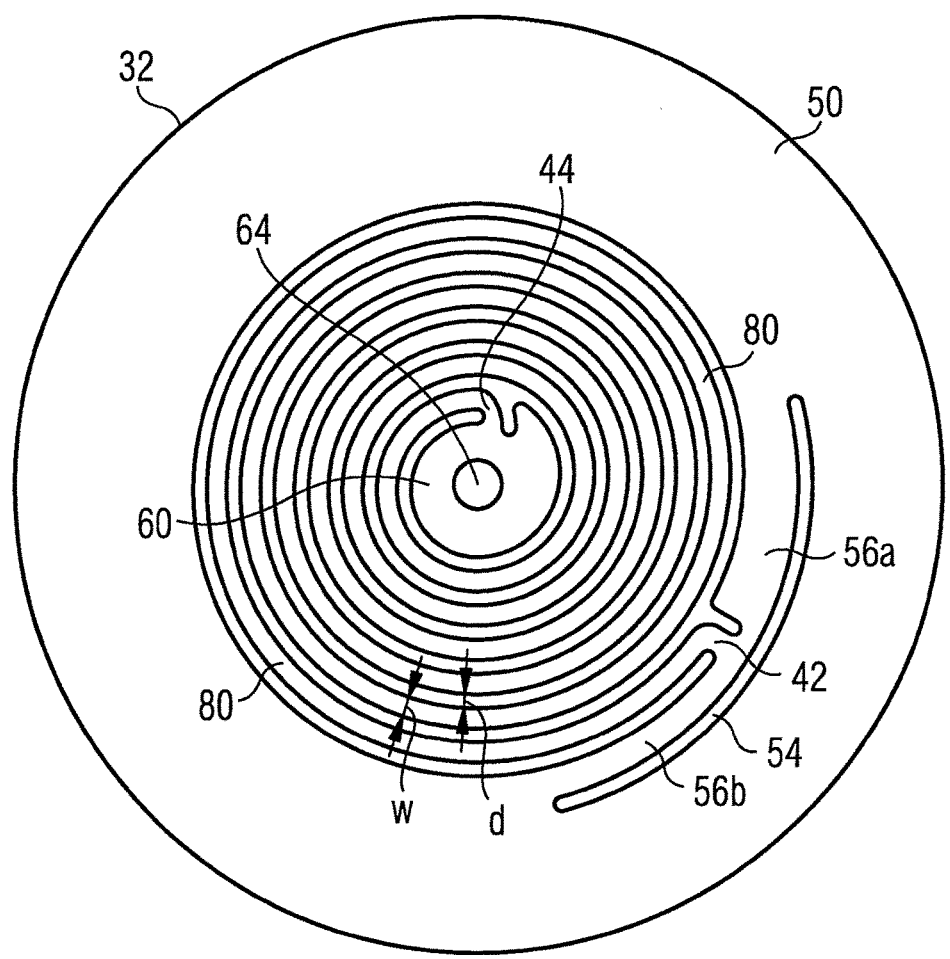
FIG. 7a shows a third embodiment of an electron beam generator according to the invention.

A third embodiment of an electron emitting device 32 is shown in FIGS. 7a and 7b. The electron emitting device in FIG. 7a looks similar to the one in FIG. 3, and the electron emitting device, of which only the spiral portion is shown, is similar to FIG. 7a but a feature has been exaggerated for visibility. The third embodiment essentially corresponds to the embodiment shown in FIG. 3 and only the differences will be described. In the preceding embodiments the spiral portion 36 has a constant width along the longitudinal extension. In this embodiment the spiral portion has instead a varying width along the longitudinal extension. In particular, an outer winding 80, being the outermost winding of the spiral portion 36, has a varying width along the longitudinal extension. The variation of the width is not easily visible to the human eye and is therefore hardly noticeable in FIG. 7a. However, in FIG. 7b, the variation has been highly exaggerated for the purpose of visibility, and to facilitate description of the varying width. The outer winding 80 is divided into angular sectors $a_1$, $a_2$, $a_3$ and $a_4$ by the imaginary lines 1, 2, 3 and 4 shown in FIG. 7b.

At the first connection portion 42 the width is $w_0$, which is the starting width and the width of the rest of the windings. The outer winding 80 in the first angular section $a_1$ has this width, i.e. the width $w_0$. In the second angular section $a_2$ the width is increasing. At the line 1 it is equal to the width $w_0$, but then the width is smoothly increasing to the line 2, where the width is $w_0+dw$. In the third angular section $a_3$ the width is constant and equal to $w_0+dw$ up to the line 3. In the fourth angular section $a_4$ the width smoothly decreases back to $w_0$ which has been reached at the line 4.

The angle between line 1 and line 2 is about 120°, the angle between line 2 and line 3 is about 40°, the angle between the line 3 and line 4 is about 100° and the angle between the line 4 and line 1 is about 100°. It should be understood that the variation of the width of the spiral portion may be made in many ways, and that FIG. 7b only shows one alternative out of many. The angles may be different and there may be more or less angular sections. Further, the width may vary not only in the outer winding but in any of the other windings. At the same time the width in the outer winding may be constant.

In this embodiment a rib 56a, near the gap 54, has a larger width than a rib 56b on the other side of the first connecting point 42. The rib 56b is also near the gap 54.

The width of the rib 56a is about twice as large as the width 56b.

REFERENCE NUMERALS 10 electron beam sterilizing device
12 housing
14 first housing portion
16 second housing portion
18 electron exit window
19 foil
20 foil support member
30 electron beam generator
32 electron emitting device
34 filament
36 spiral portion
38 winding
42 first connecting portion
44 second connecting portion
48 clearance
50 outer support element
52 inner border
54 gap
56 rib
58 connecting point
60 inner support element
62 outer border
64 hole
68 connecting point
70 support structure
72 support bar
74 support housing
80 outer winding

The invention claimed is:

1. Electron beam generator comprising
an electron emitting device adapted to emit an electron beam when heated to an elevated temperature, and
the electron emitting device comprising a filament having a spiral portion, a flat outer support element connected to an outer end of the spiral filament, and a flat inner support element connected to an inner end of the spiral filament, said inner end being radially inward of said outer end,
wherein the filament comprises a plurality of windings running between the flat outer support element and the flat inner support element, wherein a distance between the windings in a radial direction is equal to or smaller than a width in a radial direction of the windings.

2. Electron beam generator according to claim 1, wherein the electron emitting device is disc-shaped.

3. Electron beam generator according to claim 1, wherein a gap is formed in the outer support element.

4. Electron beam generator according to claim 1, wherein a distance between an outer winding of the filament and the outer support element is larger than a distance between adjacent windings of the filament.

5. Electron beam generator according to claim 1, wherein the filament comprises between three and eight windings.

6. Electron beam generator according to claim 1, wherein an outer connecting portion of the filament where the filament is connected to the outer support element is displaced in the circumferential direction relative to an inner connecting portion of the filament where the filament is connected to the inner support element.

7. Electron beam generator according to claim 1, wherein the filament comprises a connecting portion which merges into the inner support element and/or the outer support element, wherein the connecting portion comprises a bend between a radial and a circumferential direction.

8. Electron beam generator according to claim 1, wherein the spiral portion of the filament has a constant width along its longitudinal extension.

9. Electron beam generator according to claim 1, wherein the spiral portion of the filament has a varying width along its longitudinal extension.

10. Electron beam generator according to claim 9, wherein at least an outer winding of the spiral portion has a varying width along its longitudinal extension.

11. Electron beam generator according to claim 1, wherein the outer support element comprises at least one connecting point for mechanically and/or electrically connecting the electron emitting device.

12. Electron beam generator according to claim 1, wherein the inner support element comprises at least one connecting point for mechanically and/or electrically connecting the electron emitting device.

13. Electron beam sterilizing device for sterilizing a packaging container by electron beam irradiation, the electron beam sterilizing device comprising:
a housing enclosing an internal space and comprising an electron exit window, and
an electron beam generator according to claim 1 arranged in the internal space for generating an electron beam.

14. Electron beam sterilizing device for sterilizing a packaging container by electron beam irradiation, the electron beam sterilizing device comprising:
a housing enclosing an internal space, the housing possessing a longitudinal axis;
the housing comprising a first housing portion and a second housing portion positioned along the longitudinal axis of the housing, the second housing portion including one end adjacent the second housing part and an opposite end spaced from the first housing portion;
an electron beam generator positioned in the first portion of the housing, the electron beam generator including an electron-emitting device comprised of a filament and support elements that supports the filament;
the support elements including an inner support element and an outer support element;
the filament being wound in a spiral shape and including an outer end portion connected to the outer support element and an inner end portion connected to the inner support element so that the spiral shape filament is only supported by the inner and outer support elements, said inner end portion being radially inward of said outer end portion; and
an electron exit window at the opposite end of the second housing portion, the electron exit window comprising an electron transparent foil supported on a foil support member, wherein the filament comprises a plurality of windings running between the flat outer support element and the flat inner support element, and a distance between adjacent windings in a radial direction is equal to or smaller than a width of the filament in a radial direction of the windings.

15. Electron beam sterilizing device according to claim 14, further comprising a space between each adjacent winding of the spiral shape filament.

16. Electron beam sterilizing device according to claim 14, wherein the outer end portion of the filament connected to the outer support element is circumferentially displaced relative to the inner end portion of the filament connected to the inner support element.

* * * * *